(12) United States Patent
Lee et al.

(10) Patent No.: US 11,480,581 B2
(45) Date of Patent: Oct. 25, 2022

(54) COMPOSITIONS AND METHODS FOR TRACING THE DIET OF AN ANIMAL

(71) Applicant: Calysta, Inc., Menlo Park, CA (US)

(72) Inventors: Sungwon Lee, Fremont, CA (US); Allan LeBlanc, Menlo Park, CA (US)

(73) Assignee: CALYSTA, INC., Menlo Park, CA (US)

( * ) Notice: Subject to any disclaimer, the term of this patent is extended or adjusted under 35 U.S.C. 154(b) by 307 days.

(21) Appl. No.: 16/900,599

(22) Filed: Jun. 12, 2020

(65) Prior Publication Data

US 2021/0181205 A1 Jun. 17, 2021

Related U.S. Application Data

(60) Provisional application No. 62/949,289, filed on Dec. 17, 2019.

(51) Int. Cl.
| | | |
|---|---|---|
| *G01N 33/68* | (2006.01) | |
| *G01N 30/72* | (2006.01) | |
| *G01N 29/30* | (2006.01) | |
| *G01N 30/86* | (2006.01) | |

(52) U.S. Cl.
CPC ......... *G01N 33/6848* (2013.01); *G01N 29/30* (2013.01); *G01N 30/724* (2013.01); *G01N 30/8665* (2013.01); *G01N 2560/00* (2013.01)

(58) Field of Classification Search
CPC ........... G01N 33/6848; G01N 33/5088; G01N 30/724; G01N 30/7206; G01N 30/8665; G01N 29/30; G01N 2560/00; G01N 2030/8868

USPC ......................................................... 435/7.1
See application file for complete search history.

(56) References Cited

U.S. PATENT DOCUMENTS

| | | |
|---|---|---|
| 2,793,096 A | 5/1957 | Pomeroy |
| 4,999,302 A | 3/1991 | Kahler et al. |
| 5,079,168 A | 1/1992 | Amiot |
| H1430 H | 4/1995 | Apel et al. |
| 5,585,266 A | 12/1996 | Plitt et al. |
| 6,143,556 A | 11/2000 | Trachtenberg |
| 7,579,163 B2 | 8/2009 | Eriksen et al. |
| 9,005,979 B2 | 4/2015 | Smajlovic |
| 2003/0032170 A1 | 2/2003 | Ito et al. |
| 2011/0223629 A1 | 9/2011 | Glavanovic et al. |

(Continued)

FOREIGN PATENT DOCUMENTS

| | | |
|---|---|---|
| WO | 02/18617 A2 | 3/2002 |
| WO | 2016/161073 A1 | 10/2016 |

(Continued)

OTHER PUBLICATIONS

Wenger, "Traceability with Calysta's FeedKind protein," YouTube Video, May 26, 2017, URL= https://www.youtube.com/watch?v=MTAKq2u43AE download date Sep. 3, 2019. (2 pages) (Screenshot).

(Continued)

*Primary Examiner* — Kiet T Nguyen
(74) *Attorney, Agent, or Firm* — Seed Intellectual Property Law Group LLP

(57) ABSTRACT

The present disclosure provides methods of identifying or certifying an animal that consumed a traceable diet comprising a $C_1$ metabolizing microorganism.

21 Claims, 2 Drawing Sheets

(56) References Cited

U.S. PATENT DOCUMENTS

| | | | |
|---|---|---|---|
| 2011/0282587 A1* | 11/2011 | Jones | G06F 17/10 |
| | | | 702/22 |
| 2012/0323809 A1 | 12/2012 | Fukui | |
| 2014/0097338 A1* | 4/2014 | Eiler | H01J 49/04 |
| | | | 250/288 |
| 2016/0319044 A1* | 11/2016 | Opekun, Jr. | G01N 33/497 |
| 2018/0285810 A1 | 10/2018 | Ramachandran et al. | |

FOREIGN PATENT DOCUMENTS

| | | |
|---|---|---|
| WO | 2017/218978 A1 | 12/2017 |
| WO | 2018/132379 A1 | 7/2018 |
| WO | 2019/036372 A1 | 2/2019 |

OTHER PUBLICATIONS

LeBlanc,"Feedkind: The Future in Nutrition," SeaWeb Seafood Summit 2019, Bangkok, Thailand, Jun. 13, 2019, 11 pages.

LeBlanc, "FeedKind"International Aquafeed, Jun. 7, 2018, pp. 30-33.

Hussey, et al., "Rescaling the trophic structure of marine food webs," *Ecology Letters*, (2014) 17: 239-250).

Wang et al., "Know your fish: A novel compound-specific isotope approach for tracing wild and farmed salmon," *Food Chemistry* 256 (2018) pp. 380-389.

deVries, et al., "Isotopic Incorporation Rates and Discrimination Factors in Mantis Shrimp Crustaceans," *PLOS One*, 10(4), Apr. 2, 2015, pp. 1-16.

World Seafood Congress, "MSC hopeful for isotope traceability tests in wild-catch species," Undercurrent News, 2019.

O'Connell T., & Hedges, R., "Isolation and Isotopic Analysis of Individual Amino Acids From Archaeological Bone Collagen: A New Method Using RP-HPLC*" *Archaeometry* 43:3 (2001) pp. 421-438.

Stolyar et al., "Search for Systems of Genetic Exchange in Methane-Oxidizing Bacteria," *Mikrobiologiya* 64(5):686-691, 1995.

Ali et al., "Duplication of the mmoX gene in *Methylosinus sporium*: cloning, sequencing and mutational analysis," *Microbiology* 152:2931-2942, 2006.

Lloyd et al., "Heterologous expression of soluble methane monooxygenase genes in methanotrophs containing only particulate methane monooxygenase," *Archives of Microbiology* 171(6):364-370, 1999.

Motoyama et al., "Effects of the amplification of the genes coding for the L-threonine biosynthetic enzymes on the L-threonine production from methanol by a gram-negative obligate methylotroph, *Methylobacillus glycogenes*," *Appl Microbiol Biotechnol* 42:67-72, 1994.

Templeton et al., "Variable carbon isotope fractionation expressed by aerobic $CH_4$-oxidizing bacteria, " *Geochimica et Cosmochimica Acta* 70(7):1739-1752, 2006.

Deshpande, "Ethanol production from cellulose by coupled saccharification/fermentation using *Saccharomyces cerevisiae* and cellulose complex from *Sclerotiun rolfsii* UV-8 mutant," *Applied Biochemistry and Biotechnology* 36(3):227-234, 1992, (article abstract) 3 pages.

Dvergedal et al., "Selection for feed efficiency in Atlantic salmon using individual indicator traits based on stable isotope profiling" *Genet Sel Evol* (2019) 51: 13; pp. 1-14.

* cited by examiner

COMPOSITIONS AND METHODS FOR TRACING THE DIET OF AN ANIMAL

BACKGROUND

Estimates of illegal, unreported, and unregulated (IUU) seafood range between 13 and 31% of total worldwide catch. This creates an enormous challenge for regulators who want to manage seafood stocks sustainably. If the harvest rates of a seafood stock cannot be reliably monitored, then the health of the seafood stock remains unknown. Additionally, IUU fishing provides a haven for other human rights abuses of vulnerable populations, including slave labor, human trafficking, and unsafe labor practices.

Most retailers, processors, and wholesalers prohibit IUU caught fish from their shelves, warehouses and processing plants. Additionally, companies commonly prohibit slave labor and human rights abuses in their supply chains, but massive seafood fraud, mislabeling of seafood, and commingling of seafood from different sources prevent enforcement.

The only way to ensure IUU and slave labor derived seafood is kept out of the supply chain is through rigorous traceability programs. These initiatives include monitoring vessels, registration of catches with local authorities, and tracing harvested seafood as it moves from one company to another.

Seafood traceability has traditionally depended on easily falsified paper records that travel with the shipment identifying source, species, and quantity. These data have been digitized and even incorporated into digital blockchains; however, such traceability programs depend upon labels that are linked to the seafood. These labels, whether digital or physical, are not intrinsic to the seafood itself, are usually attached to the packaging, and can be tampered with or removed.

Stable isotopes are naturally occurring variants of a specific element with one or more extra neutrons. Unlike radioactive isotopes, stable isotopes do not decay into other elements and on a global basis maintain a constant ratio to the reference element over time. There has been some development in the use of stable isotope to identify food fraud. However, further innovation is needed in the use of stable isotopes for identifying food fraud involving seafood and livestock.

SUMMARY

The present disclosure provides methods of identifying or certifying an animal that consumed a traceable diet comprising a $C_1$ metabolizing microorganism.

In one aspect, the present disclosure provides a method for identifying a test animal as an animal that consumed the traceable diet.

The method for identifying a test animal as an animal that consumed the traceable diet may include:

analyzing the test sample to obtain a test sample isotopic signature comprising a test sample isotopic $\delta\ ^{13}C$ value and a test sample isotopic $\delta\ ^{15}N$ value;

comparing the test sample isotopic signature to a reference isotopic signature comprising a reference isotopic $\delta\ ^{13}C$ value and a reference isotopic $\delta\ ^{15}N$ value; and identifying the test animal as an animal that consumed the traceable diet if the test sample isotopic $\delta\ ^{13}C$ value is lower than the reference isotopic $\delta\ ^{13}C$ value, and the test sample isotopic $\delta\ ^{15}N$ value is lower than the reference isotopic $\delta\ ^{15}N$ value, wherein the reference isotopic signature is determined from a reference animal that consumed a diet lacking $C_1$ metabolizing microorganism.

The method for identifying a test animal as an animal that consumed the traceable diet may include:

(a) preparing a test sample from the test animal;

(b) analyzing the test sample to obtain a test sample isotopic signature, the isotopic signature comprising at least two isotopic values selected from a test sample isotopic $\delta\ ^{13}C$ value, a test sample isotopic $\delta\ ^{15}N$ value, and a test sample isotopic $\delta\ ^{34}S$ value;

(c) comparing the test sample isotopic signature to a reference isotopic signature that comprises at least two isotopic values selected from a reference isotopic $\delta\ ^{13}C$ value, a reference isotopic $\delta\ ^{15}N$ value, and a reference isotopic $\delta\ ^{34}S$ value; and (d) identifying the test animal as an animal that consumed the traceable diet if at least two of the following are determined: the test sample isotopic $\delta\ ^{13}C$ value is lower than the reference isotopic $\delta\ ^{13}C$ value, the test sample isotopic $\delta\ ^{15}N$ value is lower than the reference isotopic $\delta\ ^{15}N$ value, and the test sample isotopic $\delta\ ^{34}S$ value is lower than the reference isotopic $\delta\ ^{34}S$ value, In another aspect, the present disclosure provides a method for certifying an animal as having consumed the traceable diet.

The method for certifying an animal as having consumed the traceable diet may include:

feeding an animal the traceable diet;

analyzing a sample obtained from the animal to determine an isotopic signature comprising an isotopic $\delta\ ^{13}C$ value and an isotopic $\delta\ ^{15}N$ value; and certifying the animal as having consumed the traceable diet if the isotopic $\delta\ ^{13}C$ value is lower than a reference isotopic $\delta\ ^{13}C$ value, and the isotopic $\delta\ ^{15}N$ value is lower than a reference isotopic $\delta\ ^{15}N$ value, wherein the reference isotopic $\delta\ ^{13}C$ value, and the isotopic $\delta\ ^{15}N$ value are obtained from a reference animal that consumed a diet that lacked $C_1$ metabolizing microorganism.

The method for certifying an animal as having consumed the traceable diet may include:

feeding an animal the traceable diet;

analyzing a sample obtained from the animal to determine an isotopic signature comprising at least two of an isotopic $\delta\ ^{13}C$ value, an isotopic $\delta\ ^{15}N$ value, and an isotopic $\delta\ ^{34}S$ value; and certifying the animal as having consumed the traceable diet if at least two of the following are determined: the isotopic $\delta\ ^{13}C$ value is lower than a reference isotopic $\delta\ ^{13}C$ value, the isotopic $\delta\ ^{15}N$ value is lower than a reference isotopic $\delta\ ^{15}N$ value, and the isotopic $\delta\ ^{34}S$ value is lower than a reference isotopic $\delta\ ^{34}S$ value, wherein the reference isotopic $\delta\ ^{13}C$ value, the isotopic $\delta\ ^{15}N$ value, and the reference isotopic $\delta\ ^{34}S$ value are obtained from a reference animal that consumed a diet that lacked $C_1$ metabolizing microorganism.

Other objectives, advantages and novel features of the disclosure will become more apparent from the following detailed description.

DETAILED DESCRIPTION

Figure 1:
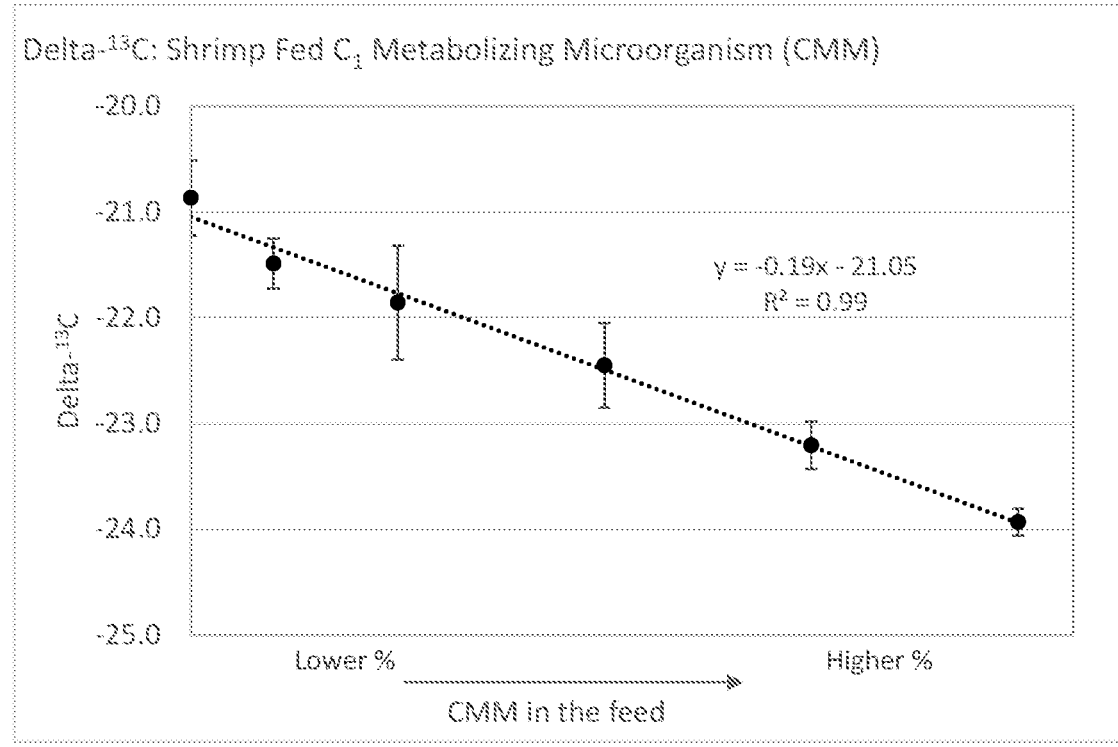
FIG. 1 is a graph of isotopic $\delta\ ^{13}C$ values obtained during a trial analyzing shrimp that consumed various concentrations of a $C_1$ metabolizing microorganism.

The instant disclosure provides methods of identifying an animal that consumed a traceable diet, and methods of certifying an animal as having consumed a traceable diet. The methods provided herein may be used for tracing the source of agricultural products such as livestock and seafood and the processed meat or fish products derived thereof.

The stable isotope approach described herein for tracing an animal (e.g., seafood or livestock) or processed meat or fish products derived thereof relies on an indelible signature that is embedded in a traceable feed provided to the animal, and then becomes incorporated into the animal itself. The traceable feed used in the methods described herein is completely harmless, cost-effective, and easily detectable via common lab equipment.

Prior to setting forth this disclosure in more detail, it may be helpful to an understanding thereof to provide definitions of certain terms to be used herein. Additional definitions are set forth throughout this disclosure.

In the present description, the term "about" means ±20% of the indicated range, value, or structure, unless otherwise indicated. The term "consisting essentially of" limits the scope of a claim to the specified materials or steps and those that do not materially affect the basic and novel characteristics of the claimed invention. It should be understood the terms "a" and "an" as used herein refer to "one or more" of the enumerated components. The use of the alternative (e.g., "or") should be understood to mean either one, both, or any combination thereof of the alternatives. As used herein, the terms "include" and "have" are used synonymously, which terms and variants thereof are intended to be construed as non-limiting. The term "comprise" means the presence of the stated features, integers, steps, or components as referred to in the claims, but that it does not preclude the presence or addition of one or more other features, integers, steps, components, or groups thereof. Any ranges provided herein include all the values and narrower ranges in the ranges.

As used herein, the term "$C_1$ substrate" refers herein to any carbon containing molecule that lacks a carbon-carbon bond. Examples include methane, methanol, formaldehyde, formic acid, carbon monoxide, carbon dioxide, a methylated amine (such as, for example, methyl-, dimethyl-, and trimethylamine), methylated thiols, methyl halogens (e.g., bromomethane, chloromethane, iodomethane, dichloromethane), cyanide, or the like.

As used herein, the term "$C_1$ metabolizing microorganism" refers to non-photosynthetic microorganisms capable of utilizing $C_1$ substrates, such as methane, natural gas, biogas, or unconventional natural gas, as its primary or sole carbon and energy source. In addition, $C_1$ metabolizing microorganisms include "obligate $C_1$ metabolizing microorganisms" that can only utilize $C_1$ substrates (e.g., methane) for carbon and energy sources, and do not utilize organic compounds that contain carbon-carbon bonds (i.e., multi-carbon-containing compounds) as a source of carbon and energy. Also included are "facultative $C_1$ metabolizing microorganisms" that are naturally able to use, in addition to $C_1$ substrates (e.g., methane), multi-carbon substrates, such as acetate, pyruvate, succinate, malate, or ethanol, as their carbon and energy source.

"Biomass" or "bacterial biomass" refers to organic material collected from bacterial culture. Biomass primarily (i.e., more than 50% w/w) comprises bacterial cells, but may include other materials such as lysed bacterial cells, bacterial cell membranes, inclusion bodies, and extracellular material (e.g., products secreted or excreted into the culture medium), or any combination thereof that are collected from bacterial fermentation along with bacterial cells. Preferably, the biomass includes more than 60%, 70%, 75%, 80%, 85%, 90% or 95% cells collected from bacterial fermentation.

As used herein, "isotopic value" (e.g., isotopic δ $^{13}$C value or isotopic δ 15N value) refers to a value of a stable isotopic composition of a low-mass (light) elements such as oxygen, hydrogen, carbon, nitrogen, and sulfur, which is reported as a "delta" (δ) values in parts per thousand (denoted as ‰) enrichment or depletion relative to a standard of known composition. The symbol ‰ is spelled out in several different ways: permil, per mil, per mill, or per mille. A δ value is calculated by:

(in ‰)=($R_{sample}$/$R_{standard}$−1)1000 where "R" is the ratio of the heavy to light isotope in the sample or standard. For example, the elements sulfur, carbon, nitrogen, and oxygen, the average terrestrial abundance ratio of the heavy to the light isotope ranges from 1:22 (sulfur) to 1:500 (oxygen); the ratio $^2$H:$^1$H is 1:6410. A positive δ value means that the sample contains more of the heavy isotope than the standard; a negative δ value means that the sample contains less of the heavy isotope than the standard. A δ 15N value of +30‰ means that there are 30 parts-per-thousand or 3% more $^{15}$N in the sample relative to the standard.

An isotopic δ $^{13}$C value refers to a value of a stable isotopic composition of carbon that is calculated by: (in ‰)=($R_{sample}$/$R_{standard}$−1)1000, where "R" is $^{13}$C:$^{12}$C. $R_{standard}$ for calculating an isotopic δ $^{13}$C value is based on the international standard Vienna Pee Dee Belmnite (VPDB).

An isotopic δ $^{15}$N value refers to a value of a stable isotopic composition of nitrogen that is calculated by: (in ‰)=($R_{sample}$/$R_{standard}$−1)1000, where "R" is $^{15}$N:$^{14}$N. $R_{standard}$ for calculating an isotopic δ $^{15}$N value is based on the atmospheric $^{15}$N:$^{14}$N ratio.

An isotopic δ $^{18}$O value refers to a value of a stable isotopic composition of oxygen that is calculated by: (in ‰)=($R_{sample}$/$R_{standard}$−1)1000, where "R" is $^{18}$O:$^{16}$O. $R_{standard}$ for calculating an isotopic δ $^{18}$O value is based on Vienna Standard Mean Ocean Water (VSMOW).

An isotopic δ $^{17}$O value refers to a value of a stable isotopic composition of oxygen that is calculated by: (in ‰)=($R_{sample}$/$R_{standard}$−1)1000, where "R" is $^{17}$O:$^{16}$O. $R_{standard}$ for calculating an isotopic δ $^{17}$O value is based on VSMOW.

An isotopic δ $^{34}$S value refers to a value of a stable isotopic composition of sulfur that is calculated by: (in ‰)=($R_{sample}$/$R_{standard}$−1)1000, where "R" is $^{34}$S:$^{32}$S. $R_{standard}$ for calculating an isotopic δ $^{34}$S value is based on Vienna-Canyon Diablo Troilite (VCDT).

An isotopic δ $^{33}$S value refers to a value of a stable isotopic composition of sulfur that is calculated by: (in ‰)=($R_{sample}$/$R_{standard}$−1)1000, where "R" is $^{33}$S:$^{32}$S. $R_{standard}$ for calculating an isotopic δ $^{33}$S value is based on VCDT.

An isotopic δ $^{36}$S value refers to a value of a stable isotopic composition of sulfur that is calculated by: (in ‰)=($R_{sample}$/$R_{standard}$−1)1000, where "R" is $^{36}$S:$^{32}$S. $R_{standard}$ for calculating an isotopic δ $^{36}$S value is based on VCDT.

An isotopic δ $^2$H value refers to a value of a stable isotopic composition of sulfur that is calculated by: (in ‰)=($R_{sample}$/

$R_{standard}$–1)1000, where "R" is $^2H:^1H$. $R_{standard}$ for calculating an isotopic δ $^2H$ value is based on VSMOW.

As used herein, "isotopic signature" refers to one or more ratios of stable isotopes of a particular element in an investigated material, as compared to an isotopic reference material. An isotopic signature may refer to a single isotopic value (e.g., an isotopic δ $^{13}C$ value) or two, three or more isotopic values (e.g., an isotopic δ $^{13}C$ value and an isotopic δ $^{15}N$ value).

A. Traceable Diet

Described herein are methods utilizing a traceable diet comprising a $C_1$ metabolizing microorganism.

In the natural world, methane has a remarkably reduced concentration of $^{13}C$ compared to a standard abundance or, in other words, a very negative δ $^{13}C$ value. The $C_1$ metabolizing microorganism of the traceable diet as provided herein derives carbon from methane and therefore maintains this ratio in its biomass. Additionally, any animal fed a traceable diet as provided herein will also reflect the lower δ $^{13}C$ value, proportional to the total carbon derived from the $C_1$ metabolizing microorganism as provided in the traceable diet.

Additionally, the $C_1$ metabolizing microorganism of the traceable diet as described herein has a surprising, measurably reduced concentration of $^{15}N$ or a very negative δ $^{15}N$ value. Thus, the traceable diets described herein will also have a very negative δ $^{15}N$ value. The $C_1$ metabolizing microorganism of the traceable diet derives nitrogen from inorganic sources and thus its δ $^{15}N$ value reflects the atmospheric reference point.

Combined, the distinctive δ $^{13}C$ value and δ $^{15}N$ value of the $C_1$ metabolizing microorganism of the traceable diet provide a surprisingly robust stable isotopic signature for tracing the source of an animal that has been fed the traceable diet.

Furthermore, a distinctive δ $^{34}S$ value of the $C_1$ metabolizing microorganism of the traceable diet allows for the use of an isotopic δ $^{34}S$ value in combination with a δ $^{13}C$ value and/or a δ $^{15}N$ value for tracing the source of an animal that has been fed the traceable diet.

As previously described, the traceable diet comprises a $C_1$ metabolizing microorganism. In certain embodiments, the $C_1$ metabolizing microorganism is a methanotrophic or methylotrophic bacterium.

"Methylotrophic bacteria" refers to any bacteria that utilize reduced carbon substrates containing no carbon-carbon bonds (such as methane, methanol, and other methylated compounds) as their sole sources of carbon and energy. "Methanotrophic bacteria" refers to any methylotrophic bacteria that have the ability to oxidize methane as its primary source of carbon and energy.

In certain embodiments, the $C_1$ metabolizing microorganism is a methylotrophic bacterium.

As used herein, "methylotroph" or "methylotrophic bacteria" refers to a bacterium that is capable of oxidizing organic compounds containing no carbon-carbon bonds, such as methane, methanol, or both. Methylotrophic bacteria include both gram-negative and gram-positive genera. The methylotrophic bacteria of the present disclosure may be aerobic methylotrophic bacteria or anaerobic methylotrophic bacteria. In certain embodiments, a methylotrophic bacterium of the present disclosure is aerobic.

Methylotrophic bacteria include facultative methylotrophs, which have the ability to oxidize organic compounds that do not contain carbon-carbon bonds (e.g., methanol), but may also utilize other carbon substrates such as sugars and complex carbohydrates, and obligate methylotrophs, which have limited to the use of organic compounds that do not contain carbon-carbon bonds. In certain embodiments, a methylotrophic bacterium is an obligate methylotroph. Illustrative obligate methylotrophs include *Methylophilus* sp., *Methylobacillus* sp., *Methylovorus* sp., and *Methylophaga* sp.

In any of the aforementioned embodiments, a $C_1$ metabolizing bacterium of this disclosure comprises particular genera of bacterial methylotrophs, such as *Methylophilus*, *Methylopila*, *Methylobacillus*, or *Methylobacterium*. Examples of methylotrophic bacteria include *Methylococcus capsulatus*, *Methylobacterium extorquens*, *Methylobacterium radiotolerans*, *Methylobacterium populi*, *Methylobacterium chloromethanicum*, *Methylobacterium nodulans*, *Methylomonas clara*, and *Methylobacillus flagellates*.

In certain embodiments, the $C_1$ metabolizing microorganism is a methanotrophic bacterium. Methanotrophic bacteria are classified into three groups based on their carbon assimilation pathways and internal membrane structure: type I (gamma proteobacteria), type II (alpha proteobacteria, and type X (gamma proteobacteria). Type I methanotrophs, such as *Methylococcus capsulatus*, use the ribulose monophosphate (RuMP) pathway for biomass synthesis and generates biomass entirely from $CH_4$, whereas a Type II methanotroph uses the serine pathway that assimilates 50-70% of the cell carbon from $CH_4$ and 30-50% from $CO_2$ (Hanson and Hanson, 1996). Type X methanotrophs use the RuMP pathway but also express low levels of enzymes of the serine pathway.

Methanotrophic bacteria are grouped into several genera, including *Methylomonas*, *Methylobacter*, *Methylococcus*, *Methylocystis*, *Methylosinus*, *Methylomicrobium*, *Methanomonas*, and *Methylocella*.

In particular embodiments, the methanotrophic bacterium is selected from the group consisting of *Methylomonas*, *Methylobacter*, *Methylococcus*, *Methylosinus*, *Methylocystis*, *Methylomicrobium*, *Methanomonas*, and *Methylocella*.

Methanotrophic bacteria include obligate methanotrophs, which can only utilize $C_1$ substrates for carbon and energy sources, and facultative methanotrophs, which naturally have the ability to utilize some multi-carbon substrates as a sole carbon and energy source. Facultative methanotrophs include some species of *Methylocella*, *Methylocystis*, and *Methylocapsa* (e.g., *Methylocella silvestris*, *Methylocella palustris*, *Methylocella tundrae*, *Methylocystis daltona* strain SB2, *Methylocystis bryophila*, *Methylocapsa aurea* KYG), and *Methylobacterium organophilum* (ATCC 27,886).

Exemplary methanotrophic bacteria species include: *Methylococcus capsulatus* Bath strain, *Methylomonas* 16a (ATCC PTA 2402), *Methylosinus trichosporium* OB3b (NRRL B-11,196), *Methylosinus sporium* (NRRL B-11, 197), *Methylocystis parvus* (NRRL B-11,198), *Methylomonas methanica* (NRRL B-11,199), *Methylomonas albus* (NRRL B-11,200), *Methylobacter capsulatus* (NRRL B-11, 201), *Methylobacterium organophilum* (ATCC 27,886), *Methylomonas* sp. AJ-3670 (FERM P-2400), *Methylocella silvestris*, *Methylocella palustris* (ATCC 700799), *Methylocella tundrae*, *Methylocystis daltona* strain SB2, *Methylocystis bryophila*, *Methylocapsa aurea* KYG, *Methylacidiphilum infernorum*, *Methylacidiphilum fumariolicum*, *Methyloacida kamchatkensis*, *Methylibium petrolelphilum*, and *Methylomicrobium alcahphilum*.

In certain embodiments, methanotrophic bacteria are aerobic methanotrophic bacteria or anaerobic methanotrophic bacteria. In particular embodiments, methanotrophic bacteria are aerobic methanotrophic bacteria. Aerobic methanotrophs can metabolize methane through a specific enzyme, methane monooxygenase (MMO).

In further embodiments, methanotrophic bacteria is *Methylococcus* (e.g., *Methylococcus capsulatus*, including the strain *Methylococcus capsulatus* Bath) or *Methylosinus* (e.g., *Methlosinus trichosporium*, including the strain *Methlosinus trichosporium* OB3b).

In particular embodiments, the $C_1$ metabolizing microorganism is *Methylococcus capsulatus*. The *Methylcoccus capsulatus* of the traceable diet may be genetically modified or non-genetically modified. In particular embodiments, *Methylcoccus capsulatus* of the traceable diet is derived from *Methylococcus capsulatus* (Bath), *Methylococcus capsulatus* (Texas), *Methylococcus capsulatus* (Aberdeen), or a combination thereof. In a preferred embodiment, *Methylcoccus capsulatus* of the traceable diet is derived from *Methylococcus capsulatus* (Bath).

In particular embodiments, the traceable diet comprises a methanotrophic bacterium and one or more heterologous non-methanotrophic bacteria. For example, a methanotrophic bacterium (e.g., Methylococcous *capsulatus* Bath) may be cultured with *Cupriavidus* sp., *Anuerinibacillus danicus*, or both and optionally in combination with *Brevibacillus agri*.

In particular embodiments, the $C_1$ metabolizing microorganism of the traceable diet is non-genetically modified.

In particular embodiments, the traceable diet comprises a modified $C_1$ metabolizing microorganism, wherein the modified $C_1$ metabolizing microorganism comprises at least one recombinant or heterologous polynucleotide that encodes a desired protein, modifies expression of an endogenous protein, or both. In particular embodiments, a recombinant or heterologous polynucleotide encoding a desired protein is operably linked to a promoter. A recombinant or heterologous polynucleotide that modifies expression of an endogenous protein may correspond to an endogenous, heterologous or synthetic regulatory element that controls expression of the endogenous protein, or it may encode a metabolic pathway enzyme whose expression results in the attenuation of expression of the endogenous protein, or the like.

A heterologous or recombinant nucleic acid molecule may be inserted into a $C_1$ metabolizing microorganism cell means transfected, transduced, transformed, electroporated, or introduction by conjugation (collectively "transformed"), wherein the nucleic acid molecule is incorporated into the genome of the cell, is extra-genomic, is on an episomal plasmid, or any combination thereof.

As used herein, the term "transformation" refers to the process of transferring a nucleic acid molecule (e.g., exogenous or heterologous nucleic acid molecule) into a host cell, which includes all methods of introducing polynucleotides into cells (such as transformation, transfection, transduction, electroporation, introduction by conjugation, or the like). The transformed host cell may carry the exogenous or heterologous nucleic acid molecule extra-chromosomally or the nucleic acid molecule may integrate into the chromosome. Integration into a host genome and self-replicating vectors generally result in genetically stable inheritance of the transformed nucleic acid molecule. Host cells containing the transformed nucleic acids are referred to as "modified," "recombinant," "non-naturally occurring," "genetically engineered," "transformed" or "transgenic" cells (e.g., bacteria).

Bacterial conjugation, which refers to a particular type of transformation involving direct contact of donor and recipient cells, is frequently used for the transfer of nucleic acids into methanotrophic bacteria. Bacterial conjugation involves mixing "donor" and "recipient" cells together in close contact with each other. Conjugation occurs by formation of cytoplasmic connections between donor and recipient bacteria, with unidirectional transfer of newly synthesized donor nucleic acid molecules into the recipient cells. A recipient in a conjugation reaction is any cell that can accept nucleic acids through horizontal transfer from a donor bacterium. A donor in a conjugation reaction is a bacterium that contains a conjugative plasmid or mobilized plasmid. The physical transfer of the donor plasmid can occur through a self-transmissible plasmid or with the assistance of a "helper" plasmid. Conjugations involving methanotrophic bacteria have been previously described in Stolyar et al., *Mikrobiologiya* 64:686, 1995; Motoyama et al., *Appl. Micro. Biotech.* 42:67, 1994; Lloyd et al., *Arch. Microbiol.* 171:364, 1999; PCT Pub. No. WO 02/18617; and Ali et al., *Microbiol./*52:2931, 2006, the methods of which are incorporated by reference herein.

In particular embodiments, the traceable diet comprises a biomass derived from whole and/or lysed cells of the $C_1$ metabolizing microorganism.

To produce a biomass derived from whole and/or lysed cells of the $C_1$ metabolizing microorganism, the $C_1$ metabolizing microorganism may be cultured with a $C_1$ substrate under a variety of culture conditions. As used herein, the term "culturing" or "cultivation" refers to growing a population of microbial cells under suitable conditions in a liquid or a solid medium. In some embodiments, culturing refers to fermentative bioconversion of a $C_1$ substrate by methanotrophic bacteria into an intermediate or an end product.

In further embodiment, the $C_1$ substrate or carbon feedstock is selected methane, methanol, syngas, natural gas, biogas, or combinations thereof. More typically, a carbon feedstock is selected from methane or natural gas. Methods for growth and maintenance of methanotrophic and methylotrophic bacterial cultures are well known in the art.

In particular embodiments, the $C_1$ metabolizing microorganism is cultured with a nitrogen source comprising inorganic nitrogen. Examples of inorganic nitrogen include $N_2$, nitrate, nitrite, and ammonium. In particular embodiments, the inorganic nitrogen comprises ammonium.

When culturing is done in a liquid culture medium, the gaseous $C_1$ substrates may be introduced and dispersed into a liquid culture medium using any of a number of various known gas-liquid phase systems as described in more detail herein below. When culturing is done on a solid culture medium, the gaseous $C_1$ substrates are introduced over the surface of the solid culture medium.

A variety of culture methodologies may be used for $C_1$ metabolizing microorganisms described herein. For example, $C_1$ metabolizing microorganisms may be grown by batch culture or continuous culture methodologies. In certain embodiments, the cultures are grown in a controlled culture unit, such as a fermenter, bioreactor, hollow fiber membrane bioreactor, or the like. Other suitable methods include classical batch or fed-batch culture or continuous or semi-continuous culture methodologies. In certain embodiments, the cultures are grown in a controlled culture unit, such as a fermenter, bioreactor, hollow fiber membrane bioreactor, and the like.

A classical batch culturing method is a closed system where the composition of the media is set at the beginning of the culture and not subject to external alterations during the culture process. Thus, at the beginning of the culturing process, the media is inoculated with the desired mutant methanotrophic bacteria and growth or metabolic activity is permitted to occur without adding anything further to the system. Typically, however, a "batch" culture is batch with respect to the addition of the methanotrophic substrate and attempts are often made at controlling factors such as pH and oxygen concentration. In batch systems, the metabolite and biomass compositions of the system change constantly up to the time the culture is terminated. Within batch cultures, cells moderate through a static lag phase to a high growth logarithmic phase and finally to a stationary phase where growth rate is diminished or halted. If untreated, cells in the stationary phase will eventually die. Cells in logarithmic growth phase are often responsible for the bulk production of end product or intermediate in some systems. Stationary or post-exponential phase production can be obtained in other systems.

The Fed-Batch system is a variation on the standard batch system. Fed-Batch culture processes comprise a typical batch system with the modification that the methanotrophic substrate is added in increments as the culture progresses. Fed-Batch systems are useful when catabolite repression is apt to inhibit the metabolism of the cells and where it is desirable to have limited amounts of the $C_1$ substrate in the media. Measurement of the actual substrate concentration in Fed-Batch systems is difficult and is therefore estimated on the basis of the changes of measurable factors, such as pH, dissolved oxygen, and the partial pressure of waste gases such as $CO_2$. Batch and Fed-Batch culturing methods are common and known in the art (see, e.g., Thomas D. Brock, Biotechnology: A Textbook of Industrial Microbiology, $2^{nd}$ Ed. (1989) Sinauer Associates, Inc., Sunderland, M A; Deshpande, *Appl. Biochem. Biotechnol.* 36:227, 1992, which methods are incorporated herein by reference in their entirety).

Continuous cultures are "open" systems where a defined culture media is added continuously to a bioreactor and an equal amount of conditioned media is removed simultaneously for processing. Continuous cultures generally maintain the cells at a constant high liquid phase density where cells are primarily in logarithmic phase growth. Alternatively, continuous culture may be practiced with immobilized cells where the $C_1$ substrate and nutrients are continuously added and valuable products, by-products, and waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limited nutrient, such as the $C_1$ substrate or nitrogen level, at a fixed rate and allow all other parameters to modulate. In other systems, a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes, as well as techniques for maximizing the rate of product formation, are well known in the art.

Liquid phase bioreactors (e.g., stirred tank, packed bed, one liquid phase, two liquid phase, hollow fiber membrane) are well known in the art and may be used for growth of microorganisms and biocatalysis.

By using gas phase bioreactors, substrates for bioproduction are absorbed from a gas by microorganisms, rather than from a liquid. Use of gas phase bioreactors with microorganisms is known in the art (see, e.g., U.S. Pat. Nos. 2,793,096; 4,999,302; 5,585,266; 5,079,168; and 6,143,556; U.S. Statutory Invention Registration H1430; U.S. Pat. Appl. Pub. No. US 2003/0032170; Emerging Technologies in Hazardous Waste Management III, 1993, eds. Tedder and Pohland, pp. 411-428, all of which are incorporated herein by reference). Exemplary gas phase bioreactors include single pass system, closed loop pumping system, and fluidized bed reactor. By utilizing gas phase bioreactors, methane or other gaseous substrates are readily available for bioconversion by polypeptides with, for example, monooxygenase activity.

Suitable fermenters for culturing $C_1$ metabolizing microorganisms (e.g., methanotrophic bacteria) may be of the loop-type or air-lift reactors. Exemplary fermenters include U-loop fermenters (see U.S. Pat. No. 7,579,163, WO2017/218978), serpentine fermenters (see WO 2018/132379), and Kylindros fermenters (see WO 2019/0366372).

In embodiments wherein the $C_1$ metabolizing microorganism is a methanotrophic bacterium, the methanotrophic bacteria may be grown as an isolated pure culture, with a heterologous non-methanotrophic bacterium that may aid with growth, or one or more different strains or species of methanotrophic bacteria may be combined to generate a mixed culture.

In embodiments where the $C_1$ metabolizing microorganism comprises *Methylcoccus capsulatus*, the traceable diet may include a biomass derived from *M. capsulatus* cultured with one or more heterologous organisms, such as *Cupriavidus* sp., *Anuerinibacillus danicus* or both and optionally in combination with *Brevibacillus agri*. In such embodiments, the bacterial biomass may comprise biomass from the heterologous organism(s) in addition to biomass from *M. capsulatus*.

In particular embodiments, the biomass comprises primarily (i.e., more than 50%, such as more than 55%, more than 60%, more than 65%, more than 70%, more than 75%, more than 80%, more than 85% or more than 90% by weight) biomass from *Methylcoccus capsulatus*.

In certain embodiments, the $C_1$ metabolizing microorganism (e.g., *Methylcoccus capsulatus*) of the traceable diet, and the related biomass, exhibit a $\delta\,^{13}C$ of less than −30‰, less than −31‰, less than −32‰, less than −33‰, less than −34‰, less than −35‰, less than −36‰, less than −37‰, less than −38‰, less than −39‰, less than −40‰, less than −41‰, less than −42‰, less than −43‰, less than −44‰, less than −45‰, less than −46‰, less than −47‰, less than −48‰, less than −49‰, less than −50‰, less than −51‰, less than −52‰, less than −53‰, less than −54‰, less than −55‰, less than −56‰, less than −57‰, less than −58‰, less than −59‰, less than −60‰, less than −61‰, less than −62‰, less than −63‰, less than −64‰, less than −65‰, less than −66‰, less than −67‰, less than −68‰, less than −69‰, or less than −70%0.

In certain embodiments, the $C_1$ metabolizing microorganism (e.g., *Methylcoccus capsulatus*) of the traceable diet, and related biomass, exhibit a $\delta\,^{13}C$ of about −35‰ to about −50‰, −45‰ to about −35‰, or about −50‰ to about −40‰, or about −45‰ to about −65‰, or about −60‰ to about −70‰, or about −30‰ to about −70%0.

In further embodiments, the *Methylcoccus capsulatus* of the traceable diet, and related biomass, exhibit a $\delta\,^{13}C$ of less than about −30‰, or ranges from about −40‰ to about −60‰, or about −40‰ to about −50%0.

In certain embodiments, the $C_1$ metabolizing microorganism (e.g., *Methylcoccus capsulatus*) of the traceable diet, and related biomass, exhibit a δ $^{15}$N of about 2‰ to about −5‰ or about −0‰ to about −3‰.

In certain embodiments, the $C_1$ metabolizing microorganism (e.g., *Methylcoccus capsulatus*) of the traceable diet, and related biomass, exhibit a δ $^{34}$S of about 5‰ to about 15‰, such as about 5‰ to about 7.5‰, about 7.5‰ to about 10‰, about 10‰ to about 12.5‰, about 12.5‰ to about 15‰, or about 11‰ to about 13.5%0.

Biomass may be harvested from bacterial culture by various techniques, such as sedimentation, centrifugation, microfiltration, ultrafiltration, and spray drying. Preferably, biomass is harvested from bacterial culture by centrifugation (e.g., at 4,000×g for 10 minutes at 10° C.). For example, a fermentation broth (cells and liquid) may be collected and centrifuged. After centrifugation, the liquid can be discarded, and the precipitated cells may be saved and optionally lyophilized.

In particular embodiments, the traceable diet comprises the $C_1$ metabolizing microorganism at a concentration of at least 0.5%, by weight (i.e., at least 0.5% of the total weight of the diet is from the $C_1$ metabolizing microorganism or its biomass). As demonstrated in the Examples provided herein, when a $C_1$ metabolizing microorganism is provided in the traceable diet at a concentration of at least 0.5%, by weight, it is possible to identify an animal that consumed the traceable diet. In some embodiments, the traceable diet comprises the $C_1$ metabolizing microorganism at a concentration of at least 0.5%, at least 1%, at least 1.5%, at least 2%, at least 2.5%, at least 3%, at least 3.5%, at least 4%, at least 4.5% or at least 5%, by weight, based on the total weight of the traceable diet.

In particular embodiments, the traceable diet comprises the $C_1$ metabolizing microorganism at a concentration within a range of 0.5% to 50%, by weight. In some embodiments, the traceable diet comprises the $C_1$ metabolizing microorganism at a concentration within a range of 0.5% to 50%, a range of 0.5% to 40%, a range of 0.5% to 30%, a range of 0.5% to 25%, or a range of 0.5% to 20%, by weight, based on the total weight of the traceable diet. In some embodiments, the traceable diet comprises the $C_1$ metabolizing microorganism at a concentration within a range of 5% to 50%, a range of 5% to 40%, a range of 5% to 30%, a range of 5% to 25%, or a range of 5% to 20%, by weight, based on the total weight of the traceable diet.

In particular embodiments, the traceable diet comprises one or more further ingredients in addition to the $C_1$ metabolizing microorganism. The further ingredients may be chosen based on the type of animal that is fed the traceable diet. In particular embodiments, the traceable diet further comprises fishmeal or fish derived products, soybean meal, soy protein concentrate or other soy derived products, wheat, wheat flour, wheat protein concentrate, or other wheat derived products, corn, corn gluten, corn protein concentrate, or other corn derived products, poultry meal or poultry derived products, fish oil, algae oil or algae derived products, rice or rice derived products, rapeseed oil, soybean oil, palm oil, or other vegetable oils, cholesterol, krill meal or krill derived products, yeast or yeast derived products, vitamins, minerals, antioxidants, preservatives, mold inhibitors, antibiotics, vaccines, or other prescribed drugs, or any combination thereof.

B. Methods

As previously described methods of identifying an animal as an animal that consumed a traceable diet comprising a $C_1$ metabolizing microorganism are provided herein. Methods of certifying an animal as having consumed a traceable diet comprising a $C_1$ metabolizing microorganism are also provided herein.

In some embodiments, the method comprises:
(a) preparing a test sample from a test animal;
(b) analyzing the test sample to obtain a test sample isotopic signature comprising a test sample isotopic δ $^{13}$C value and a test sample isotopic δ $^{15}$N value;
(c) comparing the test sample isotopic signature to a reference isotopic signature comprising a reference isotopic δ $^{13}$C value and a reference isotopic δ $^{15}$N value; and
(d) identifying the test animal as an animal that consumed the traceable diet if the test sample isotopic δ $^{13}$C value is lower than the reference isotopic δ $^{13}$C value, and the test sample isotopic δ $^{15}$N value is lower than the test sample isotopic δ $^{15}$N value.

In some embodiments, the method comprises:
(a) preparing a test sample from the test animal;
(b) analyzing the test sample to obtain a test sample isotopic signature, the isotopic signature comprising at least two isotopic values selected from a test sample isotopic δ $^{13}$C value, a test sample isotopic δ $^{15}$N value, and a test sample isotopic δ $^{34}$S value;
(c) comparing the test sample isotopic signature to a reference isotopic signature that comprises at least two isotopic values selected from a reference isotopic δ $^{13}$C value, a reference isotopic δ $^{15}$N value, and a reference isotopic δ $^{34}$S value; and
(d) identifying the test animal as an animal that consumed the traceable diet if at least two of the following are determined: the test sample isotopic δ $^{13}$C value is lower than the reference isotopic δ $^{13}$C value, the test sample isotopic δ $^{15}$N value is lower than the reference isotopic δ $^{15}$N value, and the test sample isotopic δ $^{34}$S value is lower than the reference isotopic δ $^{34}$S value,
wherein the reference isotopic signature is determined from a reference animal that consumed a diet lacking $C_1$ metabolizing microorganism.

In some embodiments, the method comprises:
(a) feeding an animal a traceable diet comprising a $C_1$ metabolizing microorganism;
(b) analyzing a sample obtained from the animal to determine an isotopic signature comprising an isotopic δ $^{13}$C value and an isotopic δ $^{15}$N value; and
(c) certifying the animal as having consumed the traceable diet if the isotopic δ $^{13}$C value is lower than a reference isotopic δ $^{13}$C value, and the isotopic δ $^{15}$N value is lower than a reference isotopic δ $^{15}$N value.

In some embodiments, the method comprises:
feeding an animal a traceable diet comprising a $C_1$ metabolizing microorganism;
analyzing a sample obtained from the animal to determine an isotopic signature comprising at least two of an isotopic δ $^{13}$C value, an isotopic δ $^{15}$N value, and an isotopic δ $^{34}$S value; and
certifying the animal as having consumed the traceable diet if at least two of the following are determined: the isotopic δ $^{13}$C value is lower than a reference isotopic δ $^{13}$C value, the isotopic δ $^{15}$N value is lower than a reference isotopic δ $^{15}$N value, and the isotopic δ $^{34}$S value is lower than a reference isotopic δ $^{34}$S value,
wherein the reference isotopic δ $^{13}$C value, the isotopic δ $^{15}$N value, and the reference isotopic δ $^{34}$S value are obtained from a reference animal that consumed a diet that lacked $C_1$ metabolizing microorganism.

In particular embodiments, the reference isotopic signature is determined from a reference animal that consumed a diet lacking a $C_1$ metabolizing microorganism. The diet lacking a $C_1$ metabolizing microorganism may be a control diet that contains the same ingredients as the traceable diet except for lacking the $C_1$ metabolizing microorganism. In particular embodiments, the control diet has a composition that is substantially identical to the traceable diet, except that the $C_1$ metabolizing microorganism is replaced with a non-$C_1$ metabolizing microorganism component, such as fishmeal.

In particular embodiments, the test animal comprises a farm-raised animal. "Farm-raised animal" refers to any animal that is raised for agricultural purposes, including domesticated animals and animals raised in confinement for human purposes. The farm-raised animal may be an aquatic animal or a non-aquatic animal. Farm-raised animals include poultry (e.g. chicken, duck, turkey, goose), cattle (e.g. cow), horse, goat, sheep, pig, rabbit, and farm-raised aquatic animals (e.g., trout, salmon, shrimp, prawns, tilapia and other freshwater and saltwater fish).

In particular embodiments, the animal is an aquatic non-filter feeding animal. The aquatic non-filter feeding animal may inhabit saltwater or freshwater. Aquatic filter feeding animals, such as clams, oysters, herring, and sardines, feed by filtering fine particles out of the water. Aquatic filter feeding animals used in aquaculture are typically farmed without a human-provided food source.

In some embodiments, the aquatic non-filter feeding animal is any aquatic non-filter feeding animal that may be used in aquaculture. Examples of aquatic non-filter feeding animals that may be used in aquaculture include non-filter feeders of the Superclass Osteichthyes, which includes saltwater bony fish and freshwater bony fish; Atlantic salmon (*Salmo salar*); Roho labeo (*Labeo rohita*); Pangas catfishes (*Pangasius* spp.); Milkfish (*Chanos chanos*); Tilapia (*Oreochromis* or *Tilapia* spp.); any fish of the order Siluriformes or Nematognathi, which include catfish; Torpedo-shaped catfishes (*Clarias* spp.); Wuchang bream (*Megalobrama amblycephala*); Rainbow trout (*Oncorhynchus mykiss*); Black carp (*Mylopharyngodon piceus*); Snakehead (*Channa argus*); any member of the family Cyprinidae, which includes carps and minnows; Grass carp (*Ctenopharyngodon idellus*); Silver carp (*Hypophthalmichthys molitrix*); Common carp (*Cyprinus carpio*); Nile tilapia (*Oreochromis niloticus*); Bighead carp (*Hypophthalmichthys nobilis*); Carassius spp.; Catla (*Catla calla*); non-filter feeding crustacean such as shrimp, prawn, crab, and lobster; Whiteleg shrimp (*Litopenaeus vannamei*); Red swamp crawfish (*Procambarus clarkii*); Chinese mitten crab (*Eriocheir sinensis*); Giant tiger prawn (*Penaeus monodon*); Oriental river prawn (*Macrobrachium nipponense*); and Giant river prawn (*Macrobrachium rosenbergii*). Additional examples of aquatic non-filter feeding fish include Japanese yellowtail (*Seriola quinqueradiata*), Mediterranean seabass (*Dicentrarchus labrax*), Mediterranean (gilthead) sea bream (*Sparus aurata*), Bluefin tuna (*Thunnus thynnus* or *Thunnus orientalis*), Channel catfish (*Ictalurus punctatus*), Longnose catfish (*Leiocassis longirostris*), Coho salmon (*Oncorhynchus kisutch*), Arctic char (*Salvelinus alpinus*), King salmon (*Oncorhynchus tshawytscha*), Barramundi (*Lates calcarifer*), Cobia (*Rachycentron canadum*), Meagre (*Argyrosomus regius*), Turbot (*Scophthalmus maximus*), Amur catfish (*Parasilurus asotus*), Japanese eel (*Anguilla japonica*), Red sea bream (*Pagrus major* and *Pagellus bogaraveo*), Largemouth bass (*Micropterus salmoides*), Yellow croaker (*Larimichthys crocea*), (snubnose) Pompano (*Trachinotus blochii*), Sturgeon (*Acipenser baerii* or other *Acipenser* spp.), Fleshy prawn (*Fenneropenaeus chinensis*), Kuruma prawn (*Penaeus japonicus*), Indian white prawn (*Penaeus indicus*), Orange spotted grouper (*Epinephelus coioides*), and Hybrid striped bass (*Morone* spp.). In certain particular embodiments, the animal is a non-filter feeding Osteichthyes or is a non-filter feeding crustacean. In some embodiments, the reference isotopic signature is from one or more commercially sourced animals. For example, isotopic signatures may be determined for multiple reference animals that did not eat the traceable diet, the reference animals being of the same species as the test animal. The isotopic signatures may be averaged in order to obtain a reference isotopic signature. For example, when the test animal is a shrimp, reference animals may be commercially available farm-raised shrimp. In particular embodiments, the commercially sourced animals were obtained from the same region as the test animal. For example, if the test animal is obtained from a shrimp farm in Indonesia or is packaged with a label indicating that the test animal was raised in Indonesia, a reference animal may include a farmed-raised shrimp that is farmed in Indonesia or that was caught in Indonesia. In particular embodiments, the commercially sourced animals were obtained from the same country as the test animal. In particular embodiments, the reference animal was hatched, raised, or harvested on the land of or in the waters of the same country as the test animal.

Certain embodiments include feeding an animal (e.g., a test animal) a traceable diet comprising a $C_1$ metabolizing microorganism. Feeding the animal may be performed for a time period sufficient for the animal possess an isotopic signature influenced by the traceable diet. The time period may be, for example, for at least three days, at least four days, at least five days, at least six days, at least one week, at least two weeks, at least three weeks, or at least one month. The time period may be dependent on the type of animal and/or the size of the animal. Feeding the animal may be performed for a time period sufficient for the animal to gain a certain amount of weight, for example, at least double in weight, at least triple in weight, or at least quadruple in weight.

In particular embodiments, the method includes preparing a sample from the animal prior to determining the isotopic signature, the preparing comprising lyophilizing and homogenizing (e.g., by grinding with a mortar and pestle, bead mill homogenizing, and ultrasonic homogenizing) at least a portion of the animal.

In certain embodiments, the sample (e.g., test sample or reference sample) is a bulk sample. A "bulk sample" as used herein refers to a sample that has not been subjected to enrichment for a specific type of compound (lipids, amino acids, DNA, etc.). The sample may be a whole animal (e.g., a whole shrimp), a portion of an animal, whole tissue (e.g., a liver), a portion of a tissue (e.g., a muscle dissection, adipose tissue, or liver tissue), or a bodily fluid (e.g., blood, hemolymph, urine).

In some embodiments, the sample (e.g., test sample or reference sample) is a compound-enriched sample. Compound-enriched examples include samples enriched for lipids, fatty acids, proteins, amino acids, DNA, sugars, etc. Compound-enriched samples may be useful for performing compound specific isotope analysis.

For lipid specific or fatty acid specific isotopic analysis, a sample may be prepared by lyophilization and homogenization of a bulk sample, followed by extraction of lipids from the sample (see, e.g., Hussey, et al., *Ecology Letters*, (2014) 17: 239-250). Lipid extraction may be performed, for example, by chloroform-methanol extraction. Fatty acids may be made suitable for gas chromatography isotope-ratio mass spectrometry following derivatization as fatty acid methyl esters (FAMEs).

For amino acid specific isotopic analysis, a sample may be prepared by lyophilization and homogenization of a bulk sample, followed by extraction of amino acids from the sample (see, e.g., Wang et al. *Food Chemistry* 256 (2018) 380-389; and Dvergedal et al. *Genet Sel Evol* (2019) 51:13; https://doi.org/10.1186/s12711-019-0455-9). The sample may be prepared by acid hydrolysis to obtain free amino acids from proteins or by ethanolic extraction of free amino acids, followed by derivatization as either methoxycarbonyl methyl esters (MOC; $^{13}$C) or N-acetyl isopropyl esters (NAIP; $^{15}$N) to produce compounds amenable to GC analysis. Alternatively, HPLC analysis may be performed, such as described in O'Connell T., & Hedges, R., *Archaeometry* 43, 3 (2001) 421-438.

In some embodiments, the method includes determining the reference isotopic δ $^{13}$C value, the reference isotopic δ $^{15}$N value, and/or the reference isotopic δ $^{34}$S value. In particular embodiments, the method further includes preparing a reference sample from at least one reference animal, and determining for the reference sample the reference isotopic signature (e.g., reference isotopic δ $^{13}$C value, the reference isotopic δ $^{15}$N value, and/or the reference isotopic δ $^{34}$S value).

In particular embodiments, the method further includes identifying the test animal as an animal that did not consume the traceable diet if the test sample isotopic δ $^{13}$C value is higher than or equal to the reference isotopic δ $^{13}$C value, and the test sample isotopic δ $^{15}$N value is higher than or equal to the reference sample isotopic δ $^{15}$N value, especially when the reference isotopic δ $^{13}$C and δ $^{15}$N values are generated from one or more control animals that consumed a control diet lacking a $C_1$ metabolizing microorganism.

In particular embodiments, the test animal is identified as an animal that did not consume the traceable diet if at least two of the following are determined: the test sample isotopic δ $^{13}$C value is higher than or equal to the reference isotopic δ $^{13}$C value, the test sample isotopic δ $^{15}$N value is higher than or equal to the reference sample isotopic δ $^{15}$N value, and a test sample isotopic δ $^{34}$S value is higher than or equal to a reference sample isotopic δ $^{34}$S value.

In some embodiments, the reference isotopic signature is derived from at least two reference animals. In particular embodiments, the reference isotopic signature is determined from at least two reference animals, and comprises a mean reference isotopic δ $^{13}$C value and a mean reference isotopic δ $^{15}$N value (and optionally, a mean reference isotopic δ $^{34}$S value). When the reference isotopic signatures are derived from multiple reference animals (e.g., animals that ate a control diet, or commercially-sourced animals that did not consume the $C_1$ metabolizing microorganism), mean reference isotopic values and associated standard deviations may be calculated.

In particular embodiments, lower than the mean reference isotopic $^{13}$C value comprises or is a value that is lower than the mean reference isotopic δ $^{13}$C value minus a standard deviation calculated from the isotopic δ $^{13}$C values of the at least two reference animals. In particular embodiments, lower than the mean reference isotopic δ $^{15}$N value comprises or is a value that is lower than the mean reference isotopic δ $^{15}$N value minus a standard deviation calculated from the isotopic δ $^{15}$N values of the at least two reference animals. In particular embodiments, lower than the mean reference isotopic δ $^{34}$S value comprises or is a value that is lower than the mean reference isotopic δ $^{34}$S value minus a standard deviation calculated from the isotopic δ $^{34}$S values of the at least two reference animals. In other words, in such embodiments, a test animal is identified as an animal that consumed a traceable diet that comprises a $C_1$ metabolizing microorganism if the test sample isotopic δ $^{13}$C value is lower than the mean reference isotopic δ $^{13}$C value minus a standard deviation calculated from the isotopic δ $^{13}$C values of the at least two reference animals, the test sample isotopic δ $^{15}$N value is lower than the mean reference isotopic δ $^{15}$N value minus a standard deviation calculated from the isotopic δ $^{15}$N values of the at least two reference animals, and optionally, the test sample isotopic δ $^{34}$S value is lower than the mean reference isotopic δ $^{34}$S value minus a standard deviation calculated from the isotopic δ $^{34}$S values of the at least two reference animals.

In certain embodiments, a test animal is identified as an animal that consumed a traceable diet that comprises a $C_1$ metabolizing microorganism if at least two of the following are determined: (1) the test sample isotopic δ $^{13}$C value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% lower than the mean reference isotopic δ $^{13}$C value minus a standard deviation calculated from the isotopic δ $^{13}$C values of the at least two reference animals, (2) the test sample isotopic δ $^{15}$N value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% lower than the mean reference isotopic δ $^{15}$N value minus a standard deviation calculated from the isotopic δ $^{15}$N values of the at least two reference animals, and (3) the test sample isotopic δ $^{34}$S value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% lower than the mean reference isotopic δ $^{34}$S value minus a standard deviation calculated from the isotopic δ $^{34}$S values of the at least two reference animals. The above description includes all combinations of at least two of: the test sample isotopic δ $^{13}$C value, the test sample isotopic δ $^{15}$N value, and the test sample isotopic δ $^{34}$S value. For example, a test animal may be identified as an animal that consumed a traceable diet that comprises a $C_1$ metabolizing microorganism if the test sample isotopic δ $^{13}$C value is at least 0.5% lower than the mean reference isotopic δ $^{13}$C value minus a standard deviation calculated from the isotopic δ $^{13}$C values of reference animals, and the test sample isotopic δ $^{15}$N value is at least 2%, (e.g., at least 2.5%, 3%, 3.5%, 4%, 4.5%, 5%, 6%, 7%, 8%, 9%, 10%, 11%, 12%, 13%, 14% or 15%) lower than the mean reference isotopic δ $^{15}$N value minus a standard deviation calculated from the isotopic δ $^{15}$N values of the at least two reference animals.

In particular embodiments, higher than the mean reference isotopic δ $^{13}$C value comprises or is a value that is higher than the mean reference isotopic δ $^{13}$C value plus a standard deviation calculated from the isotopic δ $^{13}$C values of two or more reference animals, higher than the mean reference isotopic δ $^{15}$N value comprises or is a value that is higher than the mean reference isotopic δ $^{15}$N value plus a standard deviation calculated from the isotopic δ $^{15}$N values of the two or more reference animals, and higher than the mean reference isotopic δ $^{34}$S value comprises or is a value that is higher than the mean reference isotopic δ $^{34}$S value plus a standard deviation calculated from the isotopic δ $^{34}$S values of the two or more reference animals. In such embodiments, a test animal may be identified as an animal that has not consumed a traceable diet that comprises a $C_1$ metabolizing microorganism if at least two of the following are determined: (1) the test sample isotopic δ $^{13}$C value is higher than the mean reference isotopic δ $^{13}$C value plus a standard deviation calculated from the isotopic δ $^{13}$C values of two or more reference animals, (2) the test sample isotopic δ $^{15}$N value is higher than the mean reference isotopic δ $^{15}$N value plus a standard deviation calculated from the isotopic δ $^{15}$N values of the two or more reference animals, and (3) the test sample isotopic δ $^{34}$S value is higher than the mean reference isotopic δ $^{34}$S value plus a standard deviation calculated from the isotopic δ $^{34}$S values of the two or more reference animals.

In certain embodiments, a test animal is identified as an animal as not having consumed a traceable diet that comprises a $C_1$ metabolizing microorganism if at least two of the following are determined: (1) the test sample isotopic δ $^{13}$C value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% higher than the mean reference isotopic δ $^{13}$C value plus a standard deviation calculated from the isotopic δ $^{13}$C values of reference animals, (2) the test sample isotopic δ $^{15}$N value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% higher than the mean reference isotopic δ $^{15}$N value plus a standard deviation calculated from the isotopic δ $^{15}$N values of the reference animals, and (3) the test sample isotopic δ $^{34}$S value is at least 0.5%, 1%, 1.5%, 2%, 2.5%, 3%, 3.5%, 4%, 4.5%, 5%, 6%, 7%, 8%, 9%, 10%, 11%, 12%, 13%, 14% or 15% higher than the mean reference isotopic δ $^{34}$S value plus a standard deviation calculated from the isotopic δ $^{34}$S values of the reference animals. The above description includes all combinations of at least two of: the test sample isotopic δ $^{13}$C value, the test sample isotopic δ $^{15}$N value, and the test sample isotopic δ $^{34}$S value. For example, a test animal may be identified as an animal that have not consumed a traceable diet that comprises a $C_1$ metabolizing microorganism if the test sample isotopic δ $^{13}$C value is at least 0.5% higher than the mean reference isotopic δ $^{13}$C value plus a standard deviation calculated from the isotopic δ $^{13}$C values of reference animals, and the test sample isotopic δ $^{15}$N value is at least 2%, (e.g., at least 2.5%, 3%, 3.5%, 4%, 4.5%, 5%, 6%, 7%, 8%, 9%, 10%, 11%, 12%, 13%, 14% or 15%) higher than the mean reference isotopic δ $^{15}$N value plus a standard deviation calculated from the isotopic δ $^{15}$N values of the reference animals.

In some embodiments, the isotopic signatures described herein include at least two of: an isotopic δ $^{13}$C value, an isotopic δ $^{15}$N value, and an isotopic δ $^{34}$S value. In particular embodiments, the isotopic signature includes: (1) an isotopic δ $^{13}$C value and an isotopic δ $^{15}$N value, (2) an isotopic δ $^{13}$C value and an isotopic δ $^{34}$S value, or (3) an isotopic δ $^{15}$N value and an isotopic δ $^{34}$S value.

In some embodiments, the isotopic signatures described herein include an isotopic δ $^{13}$C value and an isotopic δ $^{15}$N value. In some embodiments, the isotopic signature further comprises an isotopic δ $^{17}$O value, an isotopic δ $^{18}$O value, an isotopic δ $^{33}$S value, an isotopic δ $^{34}$S value, an isotopic δ $^{36}$S value, and/or an isotopic δ $^{2}$H value.

In particular embodiments, the isotopic signature further comprises an isotopic δ $^{18}$O value. The $C_1$ metabolizing microorganisms used in the traceable diet have δ $^{18}$O value that is equivalent to the atmospheric background. Organically bound oxygen is typically heavier than the atmospheric background because the increased mass makes evaporation and exhalation by plants less likely. Depending on the geographic source of different agricultural commodities and the cellular pathway, diet ingredients have different δ $^{18}$O values. In particular embodiments, an animal is identified or certified as having consumed the traceable diet if the isotopic δ $^{13}$C value is lower than a reference isotopic δ $^{13}$C value, the isotopic δ $^{15}$N value is lower than a reference isotopic δ 15N value, and the isotopic δ $^{18}$O value is different from a reference isotopic δ $^{18}$O value. In particular embodiments, the isotopic signature further comprises an isotopic δ $^{33}$S value. In particular embodiments, an animal is identified or certified as having consumed the traceable diet if the isotopic δ $^{13}$C value is lower than a reference isotopic δ $^{13}$C value, the isotopic δ $^{15}$N value is lower than a reference isotopic δ 15N value, and the isotopic δ $^{33}$S value is different from a reference isotopic δ $^{33}$S value. In particular embodiments, an animal is identified or certified as having consumed the traceable diet if the isotopic δ $^{13}$C value is lower than a reference isotopic δ $^{13}$C value, the isotopic δ $^{15}$N value is lower than a reference isotopic δ 15N value, and the isotopic δ $^{34}$S value is lower than a reference isotopic δ $^{34}$S value. In particular embodiments, an animal is identified or certified as having consumed the traceable diet if the isotopic δ $^{13}$C value is lower than a reference isotopic δ $^{13}$C value, the isotopic δ $^{15}$N value is lower than a reference isotopic δ $^{15}$N value, and the isotopic δ $^{2}$H value is different from a reference isotopic δ $^{2}$H value.

In certain other embodiments, the isotopic signatures described herein may include an isotopic δ $^{13}$C value and an isotopic δ $^{34}$S value. In some embodiments, the isotopic signature further comprises an isotopic δ $^{15}$N value, an isotopic δ $^{17}$O value, an isotopic δ $^{18}$O value, an isotopic δ $^{33}$S value, an isotopic δ $^{36}$S value, and/or an isotopic δ $^{2}$H value.

In certain other embodiments, the isotopic signatures described herein may include an isotopic δ $^{15}$N value and an isotopic δ $^{34}$S value. In some embodiments, the isotopic signature further comprises an isotopic δ $^{13}$C value, an isotopic δ $^{17}$O value, an isotopic δ $^{18}$O value, an isotopic δ $^{33}$S value, an isotopic δ $^{36}$S value, and/or an isotopic δ $^{2}$H value.

Isotopic signatures may be measured by isotope ratio mass spectrometry. Methods of measuring isotopes are provided in, for example, Templeton et al. Geochim. Cosmochim. Acta 70:1739, 2006, which methods are hereby incorporated by reference in their entirety.

In certain embodiments, the isotopic signatures are determined from a bulk test sample (e.g., muscle of a test sample) and one or more bulk reference samples (e.g., muscle of reference samples). An exemplary method for determining isotopic signatures is provided below in Example 1.

In certain other embodiments, the isotopic signatures are determined by compound specific isotope analysis. Compound specific isotope analysis may be used to analyze an isotopic signature of, for example, a particular amino acid (e.g., glutamic acid, aspartic acid, leucine, tryptophan, tyrosine, or phenylalanine), a subset of amino acids (e.g., glutamic acid, aspartic acid, and leucine), total amino acids, total lipids or total fatty acids, saturated or unsaturated fatty acids, particular chain lengths of amino acid (e.g., C16 or C18), particular fatty acids (e.g., palmitic acid, stearic acid, palmitoleic acid), n-alkanes, or targeted hydrocarbons (e.g., isoprenoids, vitamins).

For example, the isotopic signature of specific amino acids and fatty acids derived from a test animal can be used to identify an animal that consumed the traceable diet comprising a $C_1$ metabolizing microorganism. In particular embodiments, the isotopic signatures are determined from an amino acid comprising glutamic acid, aspartic acid, leucine, tryptophan, tyrosine, phenylalanine, or a combination thereof. Glutamic acid, aspartic acid and leucine are abundant amino acids in $C_1$ metabolizing microorganisms.

Additionally amino acids enriched for carbon, such as tryptophan, tyrosine and phenylalanine can be used to identify animals fed a traceable diet comprising a $C_1$ metabolizing microorganism. In particular embodiments, the isotopic signatures are determined from one or more saturated or unsaturated fatty acids, such as those comprising C16 or C18. Exemplary fatty acids from which the isotopic signatures may be determined comprise fatty acids that are abundant in $C_1$ metabolizing microorganisms, such as palmitic acid, stearic acid, palmitoleic acid, or a combination thereof.

In some embodiments, the methods include certifying an animal as having consumed a traceable diet. Certifying the animal may include labelling a package containing at least a portion of the animal or entering information into a database to indicate that the animal consumed the traceable diet.

In certain embodiments, after the isotopic signatures are determined, the isotopic signatures are stored using one or more blockchain ledgers. Blockchain ledgers are tamper resistant digital ledgers implemented in a distributed fashion and typically without a central authority controlling the ledgers. Blockchain ledgers allow a community of users to record transactions in shared ledgers, and the transactions may not be changed/tampered with once published. Methods of operating a blockchain ledger are described, for example in PCT Patent Publication WO 2016/161073.

EXAMPLES

Example 1

Isotopic Signatures of Shrimp that have Consumed a Traceable Diet Comprising a $C_1$ Metabolizing Microorganism: Trial 1

In the following example, a first trial was designed using shrimp to demonstrate that isotopic δ $^{13}$C values and isotopic δ $^{15}$N values may be used in combination to identify animals that have consumed a traceable diet comprising a $C_1$ metabolizing microorganism. For the trial, six different shrimp feeds (diets 1-6) were formulated with 0%, 1.5%, 3.75%, 7.5%, 11.25%, or 15% of the diet being a biomass derived from the methanotrophic bacteria *Methylococcus capsulatus*. The ingredients of diets 1-6 are show in Table 1.

TABLE 1

| Ingredients | 1 | 2 | 3 | 4 | 5 | 6 |
| --- | --- | --- | --- | --- | --- | --- |
| CMM | 0.00 | 1.50 | 3.75 | 7.50 | 11.25 | 15.00 |
| Fish meal (FM), menhaden special | 15.00 | 13.50 | 11.25 | 7.50 | 3.75 | 0.00 |
| Alginate | 2.00 | 2.00 | 2.00 | 2.00 | 2.00 | 2.00 |
| Calcium carbonate | 2.00 | 2.00 | 2.50 | 2.50 | 2.50 | 3.00 |
| Cellulose | 1.00 | 1.00 | 1.00 | 1.00 | 1.00 | 1.00 |
| Cholesterol | 0.20 | 0.20 | 0.20 | 0.20 | 0.20 | 0.20 |
| Diatomaceous earth | 2.00 | 2.00 | 2.00 | 2.00 | 2.00 | 2.00 |
| Potassium Chloride | 2.00 | 2.00 | 2.00 | 2.00 | 2.00 | 2.00 |
| Krill meal | 10.00 | 10.00 | 10.00 | 10.00 | 10.00 | 10.00 |
| Magnesium oxide | 1.50 | 1.50 | 1.50 | 1.50 | 1.50 | 1.50 |
| NaCl | 0.50 | 0.50 | 0.50 | 0.50 | 0.50 | 0.50 |
| Menhaden fish oil (OP) | 0.31 | 0.44 | 0.46 | 0.82 | 1.22 | 1.50 |
| Soy lecithin (dry) | 4.00 | 4.00 | 4.00 | 0.00 | 0.00 | 0.00 |
| Monocalcium phosphate | 3.00 | 3.00 | 3.50 | 4.00 | 4.00 | 4.50 |
| Soybean 90% | 7.90 | 7.90 | 7.90 | 7.90 | 7.50 | 7.50 |
| Squid muscle meal, 84% | 15.00 | 15.00 | 14.44 | 14.90 | 15.00 | 15.00 |
| Wheat starch | 26.59 | 26.46 | 26.00 | 24.89 | 24.79 | 23.60 |
| Mineral premix-G | 4.00 | 4.00 | 4.00 | 4.00 | 4.00 | 4.00 |
| Vitamin premix-G | 3.00 | 3.00 | 3.00 | 3.00 | 3.00 | 3.00 |
| Soy lecithin (liquid) | 0.00 | 0.00 | 0.00 | 3.80 | 3.80 | 3.70 |
| Total | 100.00 | 100.00 | 100.00 | 100.00 | 100.00 | 100.00 |

CMM = $C_1$ metabolizing microorganism

Figure 2:
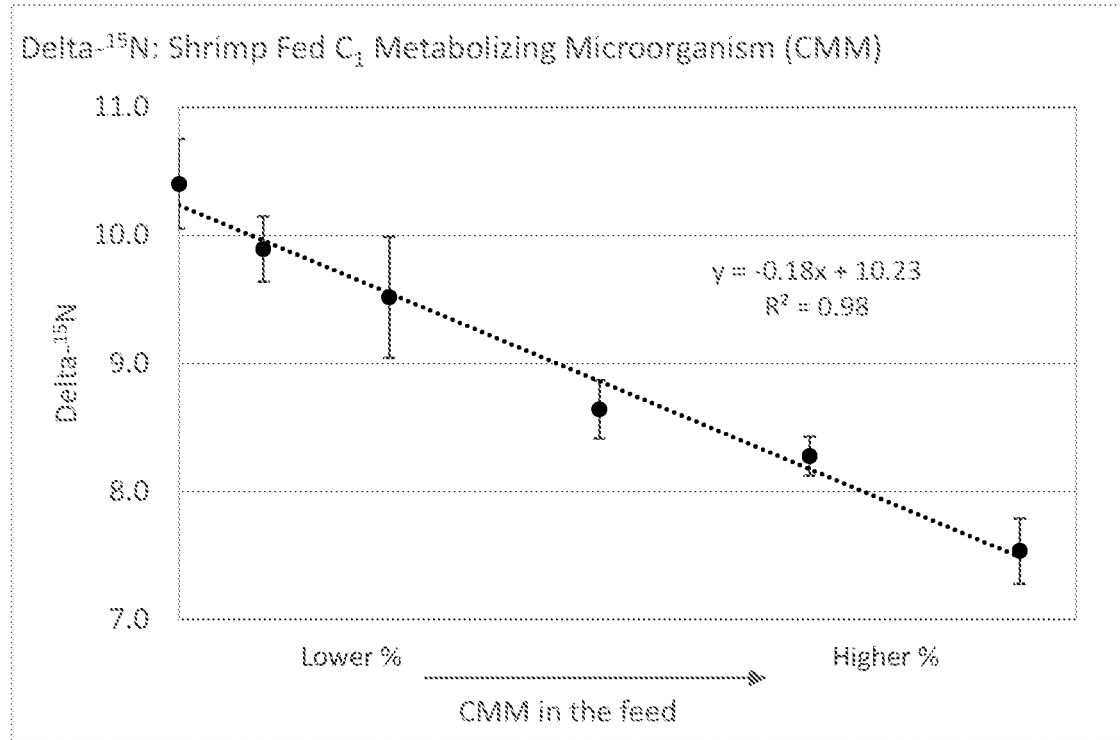
FIG. 2 is a graph of isotopic δ $^{15}$N values obtained during a trial analyzing shrimp that consumed various concentrations of a $C_1$ metabolizing microorganism.

Groups of five to six tanks containing ten shrimp each (*Litopenaeus vannamei*) were assigned to one of the diet groups. At the start of the experiment the shrimp weighed approximately 0.9 grams, and the weights were monitored at the end of the experiment. Five shrimp from each of the six diet groups were harvested for analysis when their weights reached 8-10 grams. The shrimp were dried by lyophilization followed by grinding for the isotope analysis. The ground shrimp samples were analyzed for $^{13}$C and $^{15}$N isotopes using a PDZ Europa ANCA-GSL elemental analyzer interfaced to a PDZ Europa 20-20 isotope ratio mass spectrometer. Samples were combusted at 1000° C. in a reactor packed with chromium oxide and silvered copper oxide. Following combustion, oxides were removed in a reduction reactor and the helium carrier then flows through a water trap. $N_2$ and $CO_2$ were separated on a Carbosieve GC column before entering the IRMS. During analysis, samples were interspersed with several replicates of laboratory reference materials. These reference materials had been previously calibrated against international reference materials. For each sample, a provisional isotope ratio was measured relative to a reference gas peak analyzed with each sample. These provisional values were finalized by correcting the values for the entire batch based on the known values of the included laboratory reference materials. The δ $^{13}$C values for the groups of shrimp that consumed controlled diets (diets 1-6) are shown in FIG. 1. The δ $^{15}$N values for the groups of shrimp that consumed diets 1-6 are shown in FIG. 2. The results demonstrate that as the amount of the $C_1$ metabolizing microorganism is increased, the δ $^{13}$C value and the δ $^{15}$N value each decrease in a strongly linear fashion (R=0.99 for δ $^{13}$C and R=0.98 for δ $^{15}$N). The isotopic signatures determined for each of the groups of shrimp are shown in Table 2.

TABLE 2

| Diet | | | | |
|---|---|---|---|---|
| | | Average | | STDEV |
| CMM % (w/w) in feed | $\delta\ ^{13}C$ | $\delta\ ^{15}N$ | $\delta\ ^{13}C$ | $\delta\ ^{15}N$ |
| 1  0 | −20.87 | 10.40 | 0.35 | 0.35 |
| 2  1.5 | −21.49 | 9.89 | 0.23 | 0.26 |
| 3  3.75 | −21.86 | 9.51 | 0.54 | 0.47 |
| 4  7.5 | −22.45 | 8.64 | 0.40 | 0.23 |
| 5  11.25 | −23.21 | 8.27 | 0.23 | 0.15 |
| 6  15 | −23.93 | 7.53 | 0.13 | 0.25 |

CMM = $C_1$ metabolizing microorganism

Example 2

Isotopic Signatures of Shrimp that have Consumed a Traceable Diet Comprising a $C_1$ Metabolizing Microorganism: Trial 2

In the following example, a second trial was designed using shrimp to demonstrate that isotopic $\delta\ ^{13}C$ values and isotopic $\delta\ ^{15}N$ values may be used in combination to identify animals that have consumed a traceable diet comprising a $C_1$ metabolizing microorganism. For the trial seven different shrimp feeds were formulated with 0%, 0.5%, 1.5%, 10%, or 20% of the diet being a biomass derived from the methanotrophic bacteria *Methylococcus capsulatus*. The ingredients of each of the seven diets are shown in Table 3.

TABLE 3

| Ingredients | 0% CMM | 0.5% CMM | 1.5% CMM | 10% CMM | 20% CMM/ 0% FM | 20% CMM/ 10% FM | 20% CMM/ 10% FM |
|---|---|---|---|---|---|---|---|
| CMM protein | 0.000 | .500 | 1.500 | 10.00 | 20.00 | 20.00 | 10.0 |
| Fish meal (FM), menhaden special | 20.00 | 19.50 | 18.50 | 10.00 | 0.00 | 10.00 | 20.0 |
| Soy protein concentrate | 15.00 | 15.00 | 15.00 | 15.00 | 17.80 | 5.00 | 5.0 |
| Soybean meal, dfdh | 15.93 | 15.96 | 16.01 | 15.68 | 11.99 | 15.23 | 15.082 |
| Alginate | 2.00 | 2.00 | 2.00 | 2.00 | 2.00 | 2.00 | 2.00 |
| Cholesterol | 0.20 | 0.20 | 0.20 | 0.20 | 0.20 | 0.20 | 0.20 |
| Krill meal | 2.00 | 2.00 | 2.00 | 2.00 | 2.00 | 2.00 | 2.00 |
| Magnesium oxide | 1.50 | 1.50 | 1.50 | 1.50 | 1.50 | 1.50 | 1.50 |
| DL-methionine | 0.13 | 0.13 | 0.13 | 0.47 | 0.42 | 0.32 | 0.33 |
| Menhaden fish oil (OP) | 1.04 | 1.09 | 1.18 | 1.80 | 2.76 | 1.80 | 1.04 |
| Calcium Chloride | 1.70 | 1.70 | 1.70 | 2.60 | 3.71 | 3.23 | 2.10 |
| Monocalcium phosphate | 3.97 | 4.04 | 4.18 | 4.50 | 4.61 | 3.30 | 3.03 |
| Wheat flour | 29.79 | 29.64 | 29.35 | 27.50 | 27.01 | 29.00 | 30.72 |
| Cellulose | 1.75 | 1.75 | 1.75 | 1.75 | 1.00 | 1.35 | 2.00 |
| Mineral premix | 0.30 | 0.30 | 0.30 | 0.30 | 0.30 | 0.30 | 0.30 |
| Vitamin premix | 0.20 | 0.20 | 0.20 | 0.20 | 0.20 | 0.20 | 0.20 |
| Soy lecithin (dry, 97%) | 4.00 | 4.00 | 4.00 | 4.00 | 4.00 | 4.00 | 4.00 |
| Stay-C vitamin C | 0.50 | 0.50 | 0.50 | 0.50 | 0.50 | 0.50 | 0.50 |
| Total | 100.00 | 100.00 | 100.00 | 100.00 | 100.00 | 100.00 | 100.00 |

CMM = $C_1$ metabolizing microorganism

Replicate tanks containing four shrimp each were assigned to a diet group. At the start of the experiment the shrimp weight approximately 1 gram, and the weights were monitored during the experiment. Five shrimp from each of the seven diet groups were harvested for analysis when their weights reached 10 grams.

Harvesting and analysis of the isotopic signatures were performed as described in Example 1. The isotopic signatures and standard deviation determined for each of the groups of shrimp are shown in Table 4.

TABLE 4

| | Average | | STDEV | |
|---|---|---|---|---|
| CMM, FM, SPC % (w/w) | $\delta\ ^{13}C$ | $\delta\ ^{15}N$ | $\delta\ ^{13}C$ | $\delta\ ^{15}N$ |
| 0% CMM, 20% FM, 15% SPC | −23.45 | 6.50 | 0.14 | 0.08 |
| 0.5% CMM, 19.5% FM, 15% SPC | −23.64 | 6.40 | 0.36 | 0.23 |
| 1.5% CMM, 18.5% FM, 15% SPC | −23.86 | 6.09 | 0.11 | 0.16 |
| 10% CMM, 10% FM, 15% SPC | −26.31 | 4.29 | 0.02 | 0.05 |
| 20% CMM, 0% FM, 17.8% SPC | −28.47 | 2.33 | 0.42 | 0.54 |
| 20% CMM, 10% FM, 5% SPC | −28.34 | 4.66 | 0.13 | 0.20 |
| 10% CMM, 20% FM, 5% SPC | −25.81 | 6.41 | 0.25 | 0.12 |

CMM = $C_1$ metabolizing microorganism;
FM = Fishmeal;
SPC = soy protein concentrate The results demonstrate that as the amount of the $C_1$ metabolizing microorganism is increased as a replacement for fishmeal, the $\delta\ ^{13}C$ value and the $\delta\ ^{15}N$ value each decrease in a strongly linear fashion (R=0.9957 for $\delta\ ^{13}C$ and R=0.9988 for $\delta\ ^{15}N$).

Example 3

Isotopic Signatures of Trout that have Consumed a Traceable Diet Comprising a $C_1$ Metabolizing Microorganism In the following example, a trial was designed using trout to demonstrate that isotopic $\delta\ ^{13}C$ values and isotopic $\delta\ ^{15}N$ values may be used in combination to identify animals that have consumed a traceable diet comprising a $C_1$ metabolizing microorganism. For the trial, four different trout feeds were formulated: a first diet with 0% of the diet being a biomass derived from the $C_1$ metabolizing microorganism *Methylococcus capsulatus* (CMM) and 45% fishmeal (FM), a second diet with 10% CMM and 35% FM, a third diet with 20% CMM and 25% FM, and a fourth diet with 35% CMM and 10% FM.

Three replicate tanks containing ten trout each were assigned to a diet group. Once the trout were fully grown, isotopic analysis was performed for 15 trout from each group.

Harvesting and analysis of the isotopic signatures were performed as described in Example 1, except that the analysis was conducted using dried trout fillets. The isotopic signatures and standard deviation determined for each of the groups of trout are shown in Table 5.

TABLE 5

| Feed | Average | | STDEV | |
|---|---|---|---|---|
| | $\delta\ ^{13}C$ | $\delta\ ^{15}N$ | $\delta\ ^{13}C$ | $\delta\ ^{15}N$ |
| 0% CMM | −23.36 | 9.56 | 0.42 | 0.19 |
| 10% CMM | −24.96 | 8.52 | 0.22 | 0.12 |
| 20% CMM | −26.62 | 7.70 | 0.26 | 0.25 |
| 35% CMM | −29.37 | 6.61 | 0.24 | 0.24 |

CMM = $C_1$ metabolizing microorganism

The results demonstrate that as the amount of the $C_1$ metabolizing microorganism is increased, the $\delta\ ^{13}C$ value and the $\delta\ ^{15}N$ value each significantly decrease.

Example 4

Identifying Shrimp that have Consumed a Traceable Diet Comprising a $C_1$ Metabolizing Microorganism In the following example, a first blinded trial was conducted to demonstrate that isotopic $\delta\ ^{13}C$ values and isotopic $\delta\ ^{15}N$ values may be used in combination to identify animals that have consumed a traceable diet comprising a $C_1$ metabolizing microorganism.

Two batches of shrimp were prepared by a first study participant: one batch including shrimp that had been fed a diet including a $C_1$ metabolizing microorganism (*Methylococcus capsulatus*) and the other batch including shrimp that had been fed a control diet that did not include the $C_1$ metabolizing microorganism. The batches of shrimp were provided blinded to a second study participant and randomly labeled "C2" and "C3," and the second study participant performed isotopic analysis on the blinded samples to attempt to identify the batch of shrimp had been fed a diet including a $C_1$ metabolizing microorganism, based on the isotopic analysis.

Six shrimp from each of the two batches were harvested and analyzed as described in Example 1. The isotopic values determined for the two batches are provided in Table 6.

TABLE 6

| Coded Identifier of Batch | Average | | STDEV | |
|---|---|---|---|---|
| | $\delta\ ^{13}C$ | $\delta\ ^{15}N$ | $\delta\ ^{13}C$ | $\delta\ ^{15}N$ |
| C2 | −24.48 | 3.95 | 0.43 | 0.22 |
| C3 | −20.53 | 7.68 | 0.38 | 0.22 |

Based on the isotopic signature, the second study participant predicted C2 to be the batch of shrimp that had been fed the diet comprising a $C_1$ metabolizing microorganism. Next, the first study participant un-blinded the identities of the two batches and confirmed the accuracy of the prediction that batch C2 had been fed the diet comprising a $C_1$ metabolizing microorganism.

Example 5

Identifying Shrimp that have Consumed a Traceable Diet without Controlled Diet Controls In the following example, a method of identifying an animal that has consumed a traceable diet comprising a $C_1$ metabolizing microorganism, in the absence of a controlled diet reference animal, is demonstrated.

A test shrimp that has consumed an unknown diet is obtained from a country or region. The test shrimp is harvested and analyzed to obtain an isotopic signature as described in Example 1. The test shrimp isotopic $\delta\ ^{13}C$ and $\delta\ ^{15}N$ values are compared to a mean reference $\delta\ ^{13}C$ and a mean reference $\delta\ ^{15}N$ values. The mean reference isotopic values are obtained by averaging isotopic values of commercially available shrimp that were not fed a diet including the $C_1$ metabolizing microorganism and were raised in the same country or region from which the test shrimp was obtained. The test sample is identified as having consumed the $C_1$ metabolizing microorganism if the test shrimp isotopic values are each lower than the corresponding mean reference isotopic value minus a standard deviation calculated from the isotopic values of the commercially available shrimp. Examples of mean reference isotope values that have been calculated for commercially sourced shrimp raised in various countries are provided in Table 7.

TABLE 7

| | $\delta\ ^{13}C$ Ave | $\delta\ ^{13}C$ STDEV | $\delta\ ^{15}N$ Ave | $\delta\ ^{15}N$ STDEV |
|---|---|---|---|---|
| China (farm-raised) | −23.86 | 0.47 | 5.66 | 0.96 |
| Indonesia (farm-raised) | −23.18 | 0.42 | 5.45 | 0.81 |
| South America (farm-raised) | −22.40 | 0.37 | 5.44 | 0.75 |
| USA (Wild caught) | −16.41 | 0.25 | 6.25 | 0.22 |
| Argentina (Wild caught) | −17.63 | 0.84 | 14.56 | 1.14 |

Example 6

Isotope Signatures Including an Isotopic $\delta\ ^{34}S$ Value for Shrimp that have Consumed a Traceable Diet In the following example, a trial was designed using shrimp to demonstrate that an isotopic $\delta\ ^{34}S$ value may be used to identify animals that have consumed a traceable diet comprising a $C_1$ metabolizing microorganism. This study included four sample types: a first sample type of US shrimp that consumed the traceable diet, with the traceable diet replacing 100% of fishmeal in the diet (n=10); a second sample type of US shrimp that did not consume the traceable diet (n=7); a third sample type of Thailand shrimp that consumed the traceable diet (n=12); and a fourth sample type of farm-raised Thailand shrimp that did not consume the traceable diet (n=12).

The shrimp of each sample type were homogenized together to produce one sample for each group.

Harvesting and analysis of the isotopic signatures were performed as described in Example 1, except that isotopic values were also determined for $\delta\ ^{34}S$. The isotopic signatures and standard deviation determined for each of the groups of shrimp are shown in Table 8.

TABLE 8

| | $\delta\ ^{13}C$ | | $\delta\ ^{15}N$ | | $\delta\ ^{34}S$ | |
|---|---|---|---|---|---|---|
| | Average | STDEV | Average | STDEV | Average | STDEV |
| U.S.-Shrimp trial: Control feed | −20.4 | 0.0 | 10.6 | 0.1 | 14.8 | 0.0 |
| U.S.-Shrimp trial: FeedKind feed | −23.5 | 0.0 | 8.0 | 0.1 | 12.2 | 0.0 |
| Thailand Shrimp trial: FeedKind feed | −24.2 | 0.0 | 4.6 | 0.0 | 6.9 | 0.2 |
| Farm raised commercial shrimp:Thailand | −22.6 | 0.1 | 5.7 | 0.0 | 7.7 | 0.0 |

The results demonstrate that shrimp that have consumed the traceable diet including the $C_1$ metabolizing microorganism have a decreased isotopic $\delta\ ^{34}S$ value in addition to a decreased $\delta\ ^{13}C$ and a decreased $\delta\ ^{15}N$, as compared to shrimp that have not consumed the traceable diet.

While specific embodiments of the invention have been illustrated and described, it will be readily appreciated that the various embodiments described above can be combined to provide further embodiments, and that various changes can be made therein without departing from the spirit and scope of the invention.

All of the U.S. patents, U.S. patent application publications, U.S. patent applications, foreign patents, foreign patent applications and non-patent publications referred to in this specification, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

That which is claimed is:

1. A method for identifying a test animal as an animal that consumed a traceable diet comprising a $C_1$ metabolizing microorganism, the method comprising:
   (a) preparing a test sample from the test animal;
   (b) analyzing the test sample to obtain a test sample isotopic signature comprising a test sample isotopic $\delta\ ^{13}C$ value and a test sample isotopic $\delta\ ^{15}N$ value;
   (c) comparing the test sample isotopic signature to a reference isotopic signature comprising a reference isotopic $\delta\ ^{13}C$ value and a reference isotopic $\delta\ ^{15}N$ value; and
   (d) identifying the test animal as an animal that consumed the traceable diet if the test sample isotopic $\delta\ ^{13}C$ value is lower than the reference isotopic $\delta\ ^{13}C$ value, and the test sample isotopic $\delta\ ^{15}N$ value is lower than the reference isotopic $\delta\ ^{15}N$ value,
   wherein the reference isotopic signature is determined from a reference animal that consumed a diet lacking the $C_1$ metabolizing microorganism.

2. A method for identifying a test animal as an animal that consumed a traceable diet comprising a $C_1$ metabolizing microorganism, the method comprising:
   (a) preparing a test sample from the test animal;
   (b) analyzing the test sample to obtain a test sample isotopic signature, the isotopic signature comprising at least two isotopic values selected from a test sample isotopic $\delta\ ^{13}C$ value, a test sample isotopic $\delta\ ^{15}N$ value, and a test sample isotopic $\delta\ ^{34}S$ value;
   (c) comparing the test sample isotopic signature to a reference isotopic signature that comprises at least two isotopic values selected from a reference isotopic $\delta\ ^{13}C$ value, a reference isotopic $\delta\ ^{15}N$ value, and a reference isotopic $\delta\ ^{34}S$ value; and
   (d) identifying the test animal as an animal that consumed the traceable diet if at least two of the following are determined: the test sample isotopic $\delta\ ^{13}C$ value is lower than the reference isotopic $\delta\ ^{13}C$ value, the test sample isotopic $\delta\ ^{15}N$ value is lower than the reference isotopic $\delta\ ^{15}N$ value, and the test sample isotopic $\delta\ ^{34}S$ value is lower than the reference isotopic $\delta\ ^{34}S$ value,
   wherein the reference isotopic signature is determined from a reference animal that consumed a diet lacking $C_1$ metabolizing microorganism.

3. A method comprising:
   (a) feeding an animal a traceable diet comprising a $C_1$ metabolizing microorganism;
   (b) analyzing a sample obtained from the animal to determine an isotopic signature comprising at least two of: an isotopic $\delta\ ^{13}C$ value, an isotopic $\delta\ ^{15}N$ value, and an isotopic $\delta\ ^{34}S$ value; and
   (c) certifying the animal as having consumed the traceable diet if at least two of the following are determined: the isotopic $\delta\ ^{13}C$ value is lower than a reference isotopic $\delta\ ^{13}C$ value, the isotopic $\delta\ ^{15}N$ value is lower than a reference isotopic $\delta\ ^{15}N$ value, and the isotopic $\delta\ ^{34}S$ value is lower than a reference isotopic $\delta\ ^{34}S$ value,
   wherein the reference isotopic $\delta\ ^{13}C$ value, the reference isotopic $\delta\ ^{15}N$ value, and the reference isotopic $\delta\ ^{34}S$ value are obtained from a reference animal that consumed a diet that lacked $C_1$ metabolizing microorganism.

4. The method of claim 3, wherein the reference isotopic $\delta\ ^{13}C$ value, the reference isotopic $\delta\ ^{15}N$ value, and the reference isotopic $\delta\ ^{34}S$ value are values obtained from a reference animal comprising a control animal that consumed a control diet lacking $C_1$ metabolizing microorganism.

5. The method of claim 4, wherein the reference isotopic signature is from one or more commercially-sourced animals.

6. The method of claim 5, wherein the one or more commercially-sourced animals were obtained from the same region as the test animal.

7. The method of claim 3, wherein determining the isotopic signature comprises subjecting a sample derived from the animal to isotope ratio mass spectrometry.

8. The method of claim 3, further comprising preparing a sample from the animal prior to determining the isotopic signature, the preparing comprising lyophilizing and grinding at least a portion of the animal.

9. The method of claim 3, further comprising determining at least two of the reference isotopic $\delta\ ^{13}C$ value, the reference isotopic $\delta\ ^{15}N$ value, and the reference isotopic $\delta\ ^{34}S$ value.

10. The method of claim 3, wherein the traceable diet comprises the $C_1$ metabolizing at a concentration within a range of 0.5% to 50% by weight.

11. The method of claim 3, wherein the traceable diet comprises the $C_1$ metabolizing at a concentration within a range of 0.5% to 25% by weight.

12. The method of claim 3, wherein the traceable diet further comprises fishmeal or fish derived products, soybean meal, soy protein concentrate or other soy derived products, wheat, wheat flour, wheat protein concentrate, or other wheat derived products, corn, corn gluten, corn protein concentrate, or other corn derived products, poultry meal or poultry derived products, fish oil, algae oil or algae derived products, rice or rice derived products, rapeseed oil, soybean oil, palm oil, or other vegetable oils, cholesterol, krill meal or krill derived products, yeast or yeast derived products, vitamins, minerals, antioxidants, preservatives, mold inhibitors, antibiotics, vaccines, or other prescribed drugs, or any combination thereof.

13. The method of claim 3, wherein the $C_1$ metabolizing microorganism contains nitrogen derived from an inorganic source.

14. The method of claim 3, wherein the at least two of the isotopic $\delta\ ^{13}C$ value, the isotopic $\delta\ ^{15}N$ value and the isotopic $\delta\ ^{34}S$ value of the animal are from a bulk sample of the animal, and at least two of the reference isotopic $\delta\ ^{13}C$ value, the reference isotopic $\delta\ ^{15}N$ value and the reference isotopic $\delta\ ^{34}S$ value are from bulk sample(s) of one or more reference animals.

15. The method of claim 3, wherein the at least two of the isotopic $\delta\ ^{13}C$ value, the isotopic $\delta\ ^{15}N$ value of the animal, and the isotopic $\delta\ ^{34}S$ value are at least two of the isotopic $\delta\ ^{13}C$ value, the isotopic $\delta\ ^{15}N$ value, and the isotopic $\delta\ ^{34}S$ value of one or more amino acids isolated from the animal, and at least two of the reference isotopic $\delta\ ^{13}C$ value, the reference isotopic $\delta\ ^{15}N$ value, and the reference isotopic $\delta\ ^{34}S$ value are at least two of the isotopic $\delta\ ^{13}C$ value, the isotopic $\delta\ ^{15}N$ value, and the reference isotopic $\delta\ ^{34}S$ value of the one or more amino acids isolated from the one or more reference animals.

16. The method of claim 15 wherein the one or more amino acids are selected from glutamic acid, aspartic acid, leucine, tryptophan, tyrosine, and phenylalanine.

17. The method of claim 15, wherein the one or more amino acids comprises a total amino acid content of the test sample and the reference sample.

18. The method of claim 3, wherein the at least two of: the isotopic $\delta\ ^{13}C$ value, the isotopic $\delta\ ^{15}N$ value, and the isotopic $\delta\ ^{34}S$ value of the animal are at least two of the isotopic $\delta\ ^{13}C$ value, the isotopic $\delta\ ^{15}N$ value, and the isotopic $\delta\ ^{34}S$ value of a fatty acid isolated from the animal, and at least two of the reference isotopic $\delta\ ^{13}C$ value, the reference isotopic $\delta\ ^{15}N$ value, and the isotopic $\delta\ ^{34}S$ value are at least two of the isotopic $\delta\ ^{13}C$ value, the isotopic $\delta\ ^{15}N$ value, and the isotopic $\delta\ ^{34}S$ value of the fatty acid isolated from the one or more reference animals.

19. The method of claim 18, wherein the fatty acid is palmitic acid, stearic acid or palmitoleic acid.

20. The method of claim 3, wherein:
the isotopic signature of (b) comprises an isotopic $\delta\ ^{13}C$ value and an isotopic $\delta\ ^{15}N$ value, and
the certifying of (c) comprises certifying the animal as having consumed the traceable diet if the following are determined: the isotopic $\delta\ ^{13}C$ value is lower than a reference isotopic $\delta\ ^{13}C$ value and the isotopic $\delta\ ^{15}N$ value is lower than a reference isotopic $\delta\ ^{15}N$ value.

21. The method of claim 3, wherein:
the isotopic signature of (b) comprises an isotopic $\delta\ ^{13}C$ value, an isotopic $\delta\ ^{15}N$ value, and an isotopic $\delta\ ^{34}S$ value, and
the certifying of (c) comprises certifying the animal as having consumed the traceable diet if the following are determined: the isotopic $\delta\ ^{13}C$ value is lower than a reference isotopic $\delta\ ^{13}C$ value, the isotopic $\delta\ ^{15}N$ value is lower than a reference isotopic $\delta\ ^{15}N$ value, and the isotopic $\delta\ ^{34}S$ value is lower than a reference isotopic $\delta\ ^{34}S$ value.

* * * * *